US00PP09583P

United States Patent [19]

VandenBerg

[11] Patent Number: Plant 9,583

[45] Date of Patent: Jun. 18, 1996

[54] CHRYSANTHEMUM PLANT NAMED 'CHICAGO'

[75] Inventor: Cornelis P. VandenBerg, Salinas, Calif.

[73] Assignee: Yoder Brothers Inc., Barberton, Ohio

[21] Appl. No.: 525,316

[22] Filed: Sep. 7, 1995

[51] Int. Cl.[6] ..... A01H 5/00

[52] U.S. Cl. ..... Plt./74.1

[58] Field of Search ..... Plt./74.1, 82.5

[56] References Cited

U.S. PATENT DOCUMENTS

P.P. 8,223 5/1993 VandenBerg ..... Plt./74.1

*Primary Examiner*—Howard J. Locker
*Attorney, Agent, or Firm*—Foley & Lardner

[57] ABSTRACT

A Chrysanthemum plant named Chicago particularly characterized by its flat capitulum form; daisy capitulum type; red-purple ray floret color with a green disc and a distinct dark dot in the center of the disc; diameter across face of capitulum of 73 to 76 mm when fully opened; flowering response in Salinas under normal temperatures is 52 to 56 days after start of short days; plant height is 96 to 102 cm when grown in Salinas with 11 long days prior to start or short days; peduncle length of the first and the fourth laterals at flowering after removing the apical bud is 8 cm and 10 cm; production of 9 to 15 laterals, each producing one terminal flower; and uniform flowering in year round flowerings.

3 Drawing Sheets

The present invention comprises a new and distinct cultivar of chrysanthemum, botanically known as *Dendranthema grandiflora,* and referred to by the cultivar name Chicago.

Chicago, identified as B327 (92-732001), was originated from a cross made by Cornelis P. VandenBerg in a controlled breeding program in Salinas, Calif., in 1991.

The female parent of Chicago was an unnamed seedling, identified as 5418 (84-106003) and described as a flat daisy cut mum with a red ray floret color. The female parent was discarded from all programs in October of 1991.

The male parent of Chicago was an unnamed seedling, identified as 3910 (85-642001) and described as flat daisy cut mum with a dark purple ray floret color. The male parent was discarded from all programs in May of 1991.

Chicago was discovered and selected as one flowering plant within the progeny of the stated cross by Cornelis P. VandenBerg in January 1993, in a controlled environment in Salinas, Calif.

The first act of asexual reproduction of Chicago was accomplished when vegetative cuttings were taken from the initial selection in March of 1993 in a controlled environment in Salinas, Calif. by technicians working under supervision of Cornelis P. VandenBerg.

Horticultural examination of controlled flowerings of successive plantings has shown that the unique combination of characteristics as herein disclosed for Chicago are firmly fixed and are retained through successive generations of asexual reproduction. Chicago has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Chicago, which, in combination, distinguish this Chrysanthemum as a new and distinct cultivar:

1. Flat capitulum form.
2. Daisy capitulum type.
3. Red-purple ray floret color with a green disc and a distinct dark dot in the center of the disc.

4. Diameter across face of capitulum of 73 to 76 mm when fully opened.
5. Flowering response in Salinas under normal temperatures is 52 to 56 days after start of short days.
6. Plant height is 96 to 102 cm when grown in Salinas with 11 long days prior to start of short days.
7. Peduncle length of the first and the fourth laterals at flowering after removing the apical bud is 8 cm and 10 cm.
8. Production of 9 to 15 laterals, each producing one terminal flower.
9. Uniform flowering in year round flowerings.

The accompanying photographic drawings show typical inflorescence and leaf characteristics of Chicago, with the colors being as nearly true as possible with illustrations of this type.

Sheet 1 is a color photograph of Chicago grown as a single stem spray cut mum.

Sheet 2 is a black and white photograph of three views of the inflorescence of Chicago.

Sheet 3 is a black and white photograph showing the upper and under sides of the leaves of Chicago at 3 stages of development (mature, intermediate and immature).

In sheets 2 and 3 a measuring tape in centimeters has been added.

Of the commercial cultivars known to the inventor, the most similar in comparison to Chicago is the cultivar identified as Accent, disclosed in U.S. Plant Pat. No. 3,945. Reference is made to attached Chart A, which compares certain characteristics of Chicago with the same characteristics of Accent. Similar traits are ray floret color and capitulum form and type. Chicago has a green disc with a distinct dark spot in the center of the disc, with no pollen development. Accent has a yellow-green disc, without a dark spot in the center of the disc, and scant to moderate pollen development. When compared with Accent, Chicago has a smaller diameter of capitulum, a faster flowering response, a shorter peduncle length of the 4th lateral and a taller plant height, requiring less long days prior to start of short days to reach commercial plant height.

In the following description color references are made to The Royal Horticultural Society Colour Chart. The color values were determined on plant material grown as a single stem spray cut mum in Salinas, Calif. on Jul. 5, 1995.

Classification:

*Botanical.*—*Dendranthema grandiflora* cv. Chicago.
*Commercial.*—Flat daisy spray cut mum.

INFLORESCENCE

A. Capitulum:
*Form.*—Flat.
*Type.*—Daisy.
*Diameter across face.*—73 to 76 mm when fully opened.

B. Corolla of ray florets:
*Color (general tonality from a distance of three meters).*—Dark red-purple.
*Color (upper surface).*—74A.
*Color (under surface).*—74C.
*Shape.*—Straight, flat, rounded petal tip.

C. Corolla of disc florets:
*Color (mature).*—Closest to 154C.
*Color (immature).*—Closest to 144A. Center of disc closest to 178A to 178C.

D. Reproductive organs:
*Androecium.*—Present on disc florets only; no pollen.
*Gynoecium.*—Present on both ray and disc florets.

PLANT

A. General appearance:
*Height.*—96 to 102 cm when grown in Salinas with 11 long days prior to start of short days.

B. Foliage:
*Color (upper surface).*—147A.
*Color (under surface).*—147B.
*Shape.*—Deeply lobed, strongly serrated.

CHART A

| CHARACTERISTIC | CHICAGO | ACCENT |
|---|---|---|
| Ray floret color | Dark red-purple | Dark red-purple |
| Capitulum form and type | Flat daisy | Flat daisy |
| Diameter across face of capitulum | 73 to 76 mm | 79 to 89 mm |
| Flowering response | 52 to 56 days | 54 to 59 days |
| Peduncle length | | |
| 1st lateral | 8 cm | 5 to 10 cm |
| 4th lateral | 10 cm | 13 to 20 cm |
| Plant height | 96 to 102 cm | 86 to 99 cm |

COMPARISONS MADE OF PLANTS GROWN AS SINGLE STEM SPRAY CUT MUMS IN SALINAS, CALIFORNIA

What is claimed is:

1. A new and distinct Chrysanthemum plant named Chicago, as described and illustrated.

* * * * *

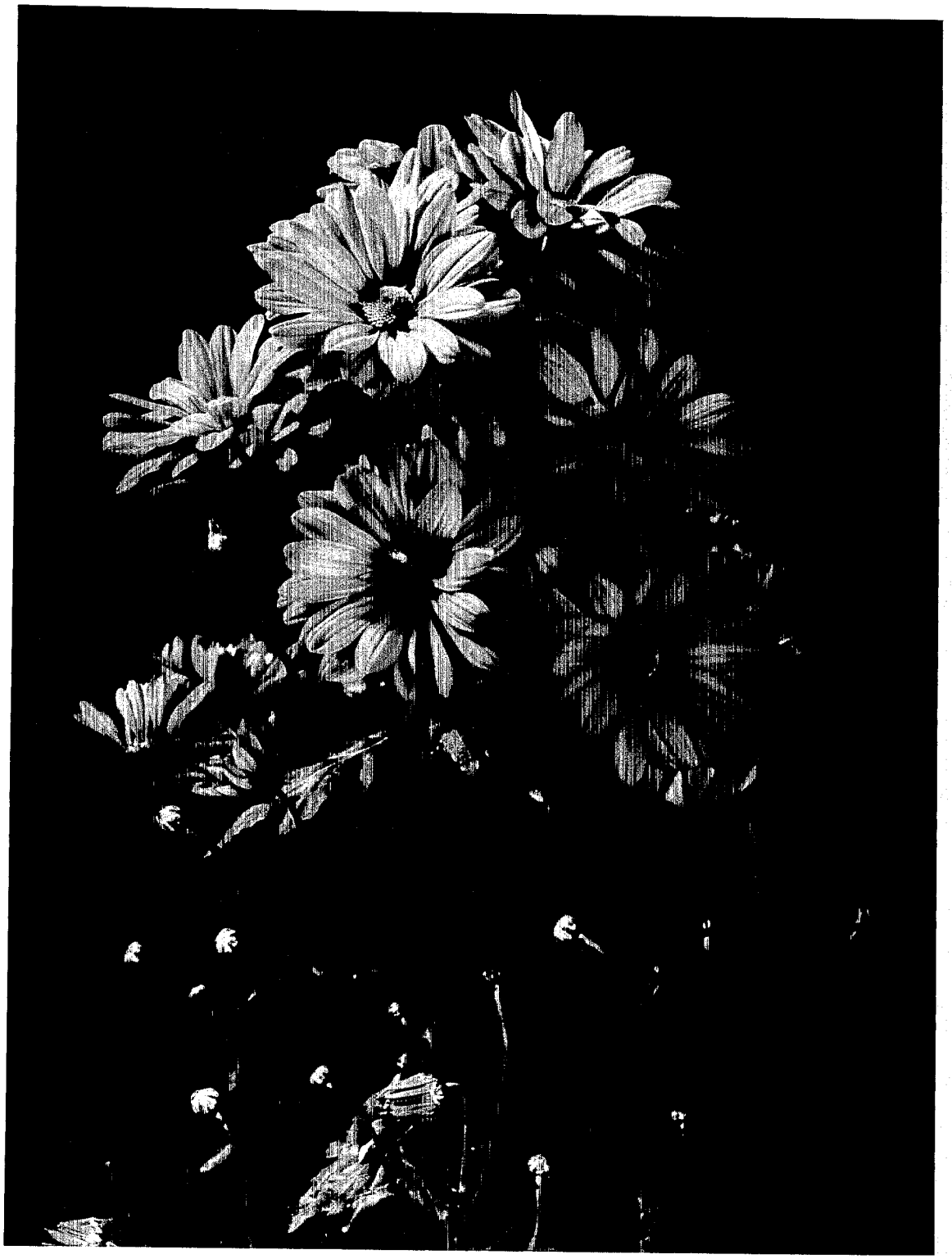

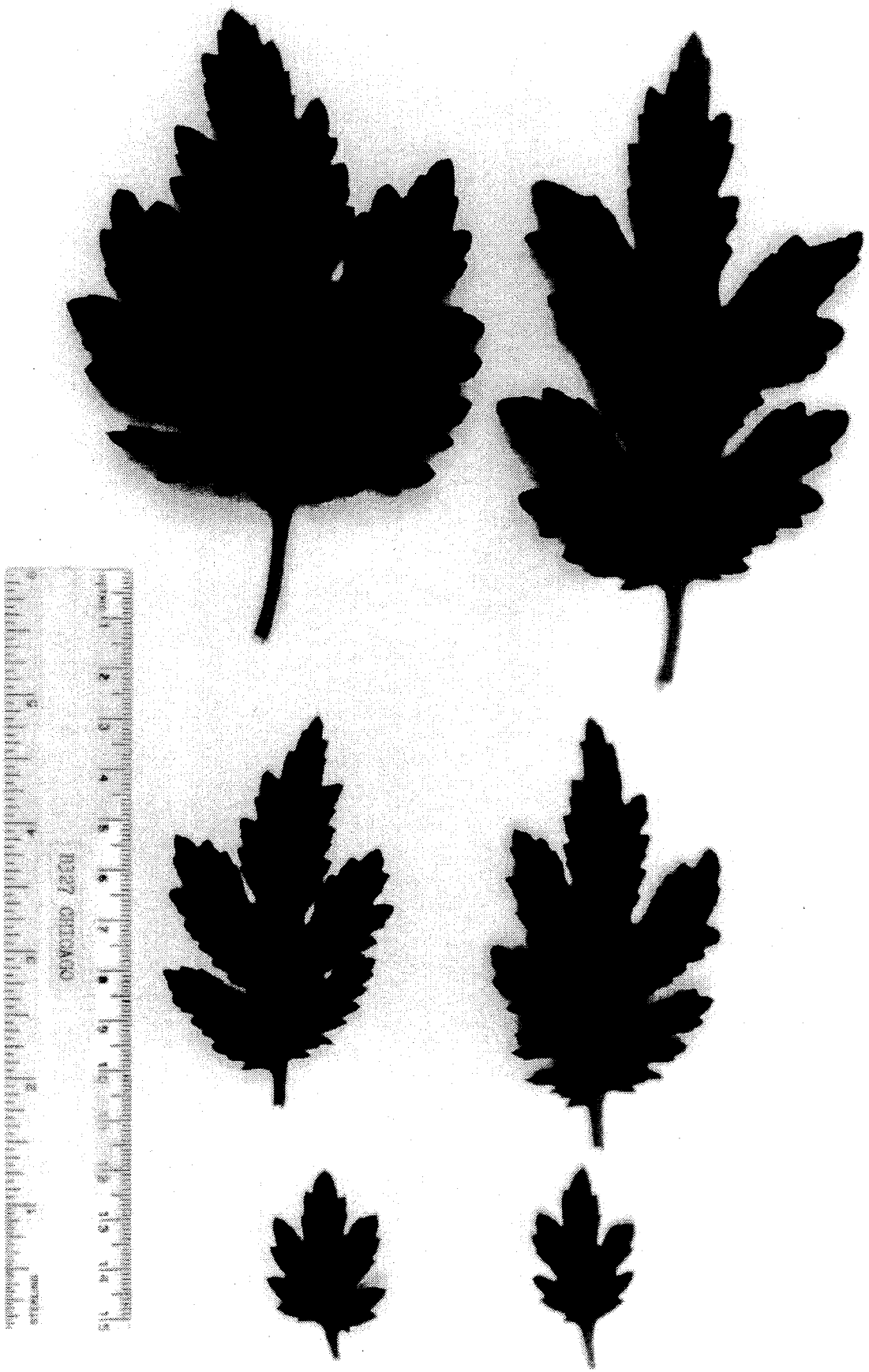

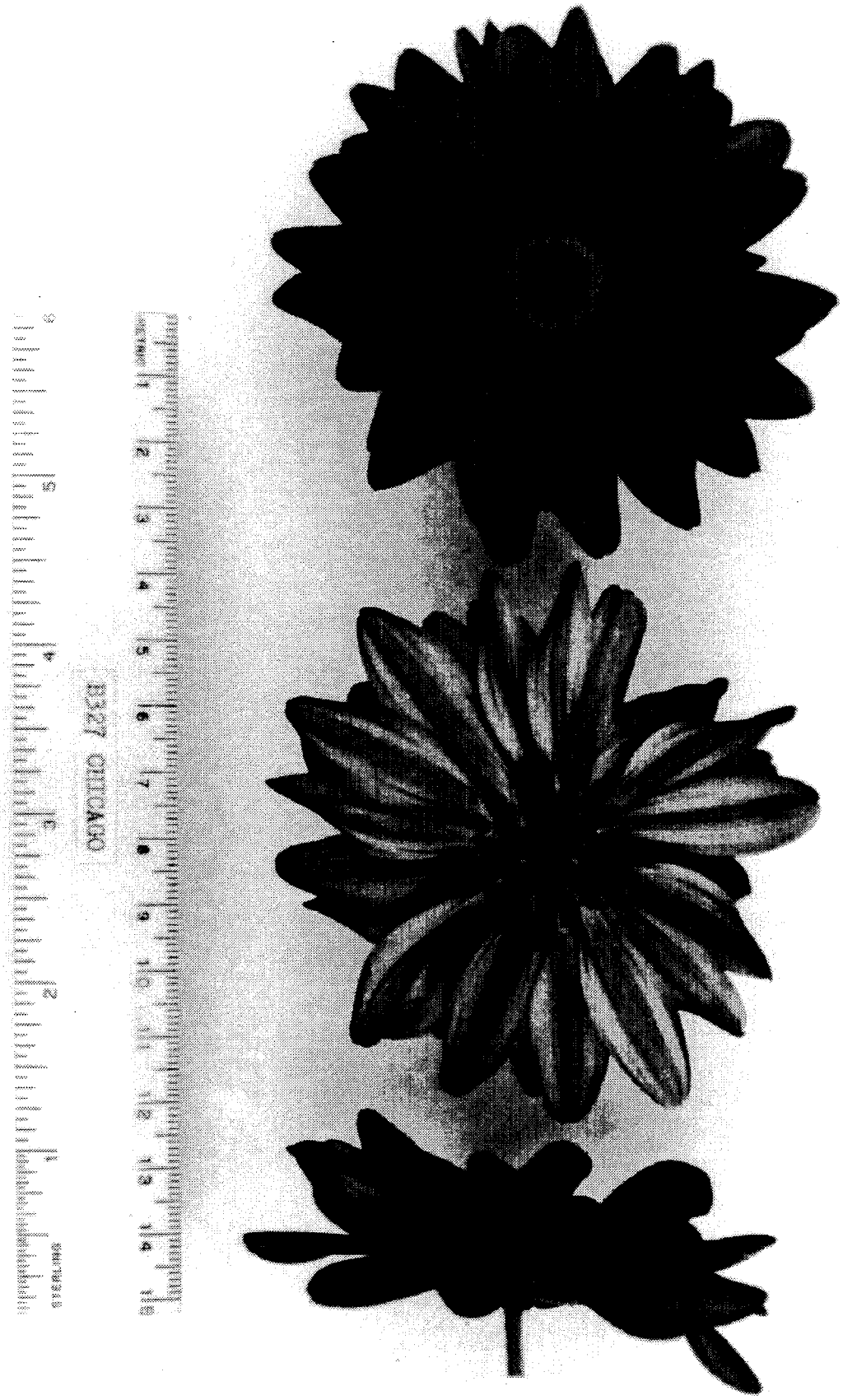
B327 CITLAMO